United States Patent
Tomalla

(10) Patent No.: US 6,228,093 B1
(45) Date of Patent: *May 8, 2001

(54) DEVICE FOR PROTECTING ORGANS OF THE EYE WHICH ARE SITUATED IN THE REGION OF THE ANTERIOR CHAMBER OF THE EYE DURING EYE LENS SURGERY

(75) Inventor: Mark Tomalla, Mühlheim (DE)

(73) Assignee: Karin Tomalla, Mühlheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/245,721

(22) Filed: Feb. 8, 1999

(30) Foreign Application Priority Data

Feb. 9, 1998 (EP) .................................. 98102224

(51) Int. Cl.[7] ................................. A61F 9/00; A61B 1/32
(52) U.S. Cl. ............................................ 606/107; 600/236
(58) Field of Search ........................... 606/107, 166; 600/236

(56) References Cited

U.S. PATENT DOCUMENTS

| | | | |
|---|---|---|---|
| 3,054,398 | * 9/1962 | Kobler | 600/236 |
| 4,387,706 | * 6/1983 | Glass | 600/236 |
| 4,959,048 | * 9/1990 | Seder et al. | 604/9 |
| 5,159,921 | * 11/1992 | Hoover | 600/236 |
| 5,374,272 | * 12/1994 | Arpa et al. | 606/107 |
| 5,433,190 | * 7/1995 | Sunlap | 600/236 |
| 5,540,699 | * 7/1996 | Smith | 606/107 |
| 5,716,328 | * 2/1998 | Grieshaber et al. | 600/206 |
| 5,817,099 | * 10/1998 | Skolik et al. | 606/107 |

* cited by examiner

Primary Examiner—Gene Mancene
Assistant Examiner—Michael B. Priddy
(74) Attorney, Agent, or Firm—Evenson, McKeown, Edwards & Lenahan, P.L.L.C.

(57) ABSTRACT

Organs of the eye which are situated in the region of the anterior chamber of the eye are protected during eye lens surgery by a device in which a surgical instrument, such as a tip of a phacoprobe, is guided to the posterior chamber of the eye through a tunnel placed in the cornea/sclera region into the anterior chamber. In order to particularly protect the iris of the eye, a push-in part is provided and can be pushed through the tunnel into the anterior chamber at a push-in length which covers the iris at least partially in the radial direction. The push-in part is connected with a holding part which can be supported outside the tunnel on the exterior surface of the eye. An area which extends in the tunnel and is used for thermal control has a smaller width than an area which projects into the anterior chamber.

6 Claims, 1 Drawing Sheet

DEVICE FOR PROTECTING ORGANS OF THE EYE WHICH ARE SITUATED IN THE REGION OF THE ANTERIOR CHAMBER OF THE EYE DURING EYE LENS SURGERY

BACKGROUND OF THE INVENTION

This invention relates to a device for protecting organs of the eye which are situated in the region of the anterior chamber of the eye during eye lens surgery by means of a tunnel placed in the cornea/sclera region in the anterior chamber.

During eye lens surgery, particularly cataract operations, in certain eye types, complications in the form of a prolapse of the iris or the loss of pigment in the tissue of the iris occur if the instrument, such as a phacoprobe, which is used in the operation, comes in contact with the tissue. These difficulties occur mainly in narrow pupils, for example, after miotic therapy or in hyperopic eyes with temporarily flat anterior chambers. The above-mentioned difficulties may also arise when a pressure is present from the rear during surgery; this may occur during local anesthesia of asthmatic patients or adipose patients.

SUMMARY OF THE INVENTION

It is therefore an object of the invention to provide a device of the initially mentioned type by which a careful treatment is achieved during eye lens surgery, particularly during a cataract operation.

According to the invention, this object is achieved by providing a device of the initially mentioned type which has a push-in part which can be pushed through the tunnel into the anterior chamber of the eye at a push-in length which at least partially but in particular essentially covers the iris. This push-in part is connected with a holding part which can be supported outside the tunnel on the exterior surface of the eye in the region of the sclera. The holding part preferably has supporting surfaces which are supported laterally of the exterior tunnel end on the exterior surface of the cornea or sclera. The push-in part and the holding part are constructed in one piece from a flexible foil and, more particularly, are punched from a foil web. The edges formed during punching are rounded off by polishing. The push-in part has a smaller width in the area which is situated inside the tunnel during the operation than at the forward end which projects approximately 3 mm into the anterior chamber. The reduction in width ensures that, during the operation, rinsing and cooling liquid, which is required during phaco-emulsification, can flow laterally through the tunnel and out. As a result of the widened forward end of the push-in part, a protection surface is made as large as possible and, during the operation, particularly during the phaco-emulsification within the scope of a cataract operation, protects the iris situated below the push-in part from contact with a surgical instrument, such as a phacoprobe, which is guided on the top side of the push-in part into the anterior chamber. This facilitates guiding of the surgical instrument, particularly of the tip of the phacoprobe, to the treatment site into the posterior chamber without contact with the iris. Since the push-in part is connected on its rearward end with the holding part, which is supported on the exterior side of the eye, fixing of the push-in part is achieved during surgery. The push-in part introduced into the anterior chamber also prevents a prolapse of the tissue of the iris through the tunnel opening.

BRIEF DESCRIPTION OF THE DRAWING

An embodiment of the invention shown in the figures will now be explained in greater detail.

DESCRIPTION OF THE PREFERRED EMBODIMENT

Figures 1, 2:
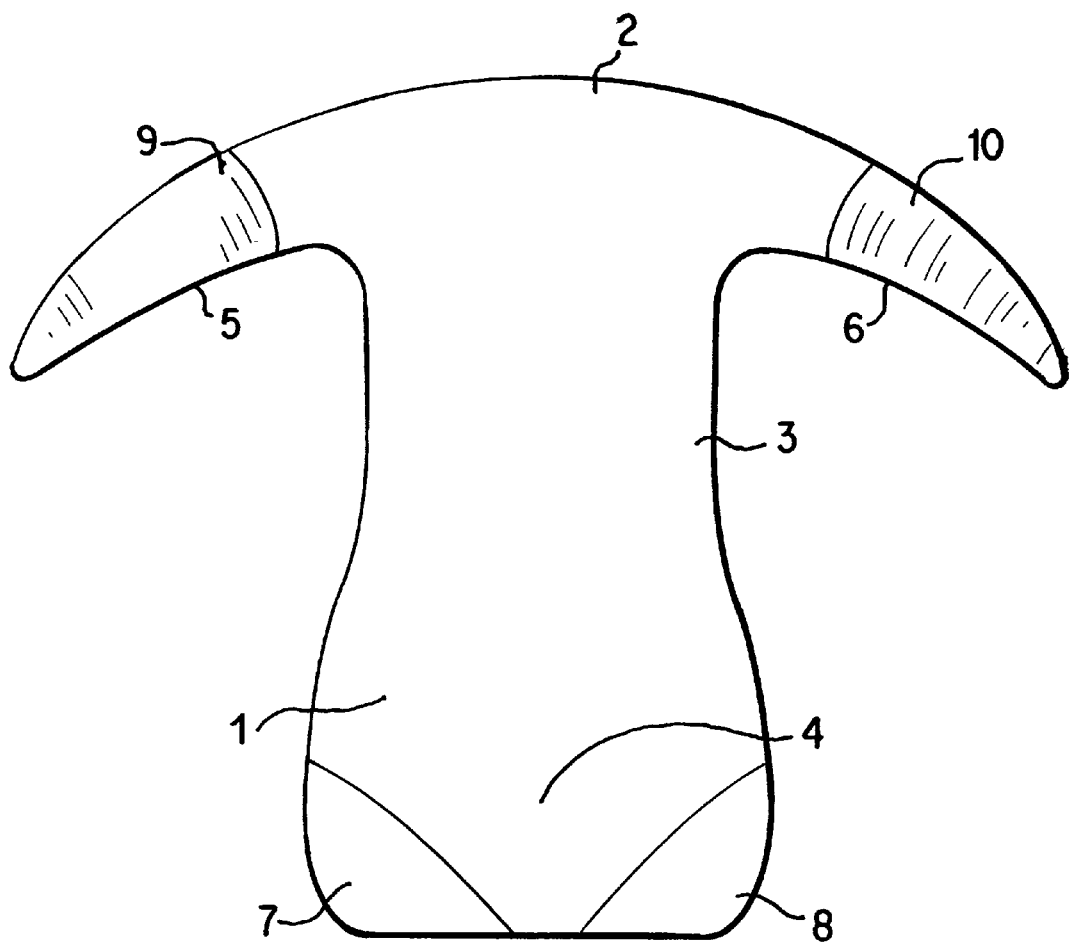
FIG. 1 is a top view of the protection device.
FIG. 2 is a view of the protection device shown in FIG. 1 as seen in the direction of arrow II.

The protection device has a push-in part 1 which can be pushed in through a tunnel placed in the cornea and, for example, in the limbus region. The length of the push-in part 1 is dimensioned such that the iris is essentially covered in the radial direction. At the rearward end, the push-in part 1 is connected with a holding part 2. By means of tweezers applied, for example, to the holding part 2, the push-in part 1 can be inserted through the tunnel into the anterior chamber, after the anterior chamber has been set by a viscoelastic material. For better slidability of the surgical instruments, such as the tip of the phacoprobe, the surface of the push-in part 1 may also be provided with a viscoelastic material. In the inserted condition, the frontal portion 4 of the push-in part is situated approximately 3 mm in the anterior chamber of the eye and covers the iris of the eye essentially in the radial direction. The width of this frontal portion is dimensioned such that movements of the surgical instrument, such as the tip of the phacoprobe, take place on the surface of the push-in part 1. The widened forward end 4 of the push-in part 1 may have a width of, for example, 3.5 mm and correspond approximately to the sectional width of the tunnel. An area 3 of the push-in part 1, which is in the corneal tunnel during the operation, has a smaller width than the area 4. This width may be approximately 3.2 mm. The tapered area 3 ensures that rinsing liquid or cooling liquid, which is used particularly during phaco-emulsification, can flow out of the tunnel unhindered. The tapered area 3 of the push-in part 1 has a smaller width than the tunnel. This prevents burns on the cornea.

The holding part 2 on the rearward end of the push-in part 1 has a significantly wider construction than the sectional opening at the tunnel end. The holding part 2 has supporting edges or supporting surfaces 5 and 6 which rest laterally of the exterior tunnel end on the exterior surface on the cornea or on the limbus. The protection device according to this embodiment is mushroom-shaped in the top view. During surgery, the device has a stabilizing effect since the tissue of the iris can be held essentially in its natural position.

For removal of the device from the eye, the device can be pulled out by tweezers which are applied to the holding part 2 situated on the outside. So that a secure support is ensured during surgery on the exterior side of the cornea by way of the supporting surfaces 5 and 6, the holding part 2 has a significantly wider construction than the tunnel opening and in the present embodiment may be, for example, 4.2 mm.

The protection device is constructed in one piece from a foil material and preferably has a thickness in the range of from 50 to 100 $\mu$m. Polyesters, such as polyethyleneterephthalate (PET), polyester caoutchouc or polytetrafluoroethylene and other temperature-stable nontoxic synthetics are suitable as foil materials. The body of the mushroom-shaped protection foil can be obtained, by punching, from a foil web. The punched edges are rounded off by polishing.

The two lateral forward edge areas 7 and 8 of the push-in part 1 have an approximately triangular shape. The foil material at the two lateral forward edge areas may have a higher stiffness and strength than in the remaining area of the foil body. In the same manner, in the area of the supporting surfaces 5 and 6, the two lateral ends 9 and 10 of the holding part 2 may have a higher stiffness and strength than the remaining foil material. The areas 7 to 10 of the foil body may have approximately the same stiffness and strength.

Particularly during phaco-emulsification, the tissue of the iris is also protected by the illustrated stabilizing protection foil with respect to thermal stress caused by the tip of the phacoprobe. The protection foil is an aid which is easy to handle during surgery in the areas of the anterior and posterior chambers of the eye, particularly when removing the natural lens of the eye by phaco-emulsification.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Device for protecting organs of an eye which are situated in a region of an anterior chamber of the eye during surgery by way of a tunnel placed in a cornea/sclera region in the anterior chamber, comprising:

a push-in part for insertion through the tunnel into the anterior chamber, said push-in part having a first area which, in an inserted position, is positioned in the tunnel, and a second area which forms a frontal portion of the push-in part and, in the inserted position, essentially covers the iris in a radial direction, said first area of the push-in part having a slightly smaller width than said second area, said second area having a width which corresponds approximately to a sectional width of the tunnel; and a holding part having supporting surfaces for supporting the holding part laterally of the exterior end of the tunnel on an exterior surface of the cornea/sclera;

wherein said holding part and said push-in part are constructed in one piece from a flexible foil of nontoxic synthetic material.

2. Device according to claim 1, wherein the push-in part has forward edge areas which have a higher stiffness than other areas of the push-in part.

3. Device according to claim 1, wherein, in areas of the supporting surfaces, the holding part has a stiffness or stability which is higher than in remaining areas of the holding part.

4. Device according to claim 1, wherein the foil consists of a heat-resistant synthetic material.

5. Device according to claim 3, wherein the foil consists of a heat-resistant synthetic material.

6. Device according to claim 2, wherein the foil consists of a heat-resistant synthetic material.

* * * * *